United States Patent [19]

Ashton et al.

[11] Patent Number: 5,114,925

[45] Date of Patent: May 19, 1992

[54] RENIN INHIBITORS CONTAINING THE 2-[[(2R,3S)-3-AMINO-4-CYCLOHEXYL-2-HYDROXY-1-BUTYL]THIO)ALKANOYL MOIETY AND THE CORRESPONDING SULFOXIDE AND SULFONE DERIVATIVES

[75] Inventors: Wallace T. Ashton, Clark; Christine L. Cantone, Hazlet; Richard L. Tolman, Warren, all of N.J.

[73] Assignee: Merck & Co., Inc., Rahway, N.J.

[21] Appl. No.: 756,632

[22] Filed: Sep. 9, 1991

Related U.S. Application Data

[63] Continuation of Ser. No. 644,412, Jan. 22, 1991, abandoned.

[51] Int. Cl.$^5$ ............................................. A61K 37/00
[52] U.S. Cl. ................................................ 514/18; 514/19
[58] Field of Search ................................................ 514/18, 19

[56] References Cited

U.S. PATENT DOCUMENTS

| | | |
|---|---|---|
| 4,609,641 | 9/1986 | Evans et al. |
| 4,616,088 | 10/1986 | Ryono et al. ............... 546/336 |
| 4,711,958 | 12/1987 | Iizuka et al. |
| 4,940,811 | 7/1990 | Peter .................................. 558/262 |

OTHER PUBLICATIONS

Burger. *Medicinal Chemistry*, 1960, pp. 565–571, 578–581, 600–601.

Denkewalter et al., *Progress In Drug Research*, vol. 10, pp. 510–512.

Plattner et al., *J. Med. Chem.* 1988, 31(12), 2277–2288.

*Primary Examiner*—Lester L. Lee
*Assistant Examiner*—E. J. Kraus
*Attorney, Agent, or Firm*—Mark R. Daniel; Hesna J. Pfeiffer

[57] ABSTRACT

Compounds of the formula:

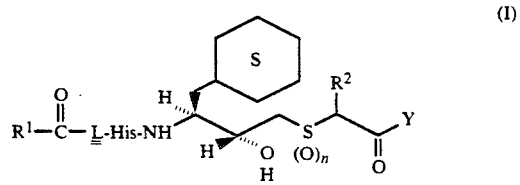

which are potent inhibitors of human renin and are useful for treating various forms of renin-associated hypertension, hyperaldosteronism and congestive heart failure; compositions containing these renin-inhibitory compounds, optionally with other antihypertensive agents; and methods of treating hypertension, hyperaldosteronism or congestive heart failure or of establishing renin as a causative factor in these conditions which employ these novel compounds.

18 Claims, No Drawings

RENIN INHIBITORS CONTAINING THE 2-[[(2R,3S)-3-AMINO-4-CYCLOHEXYL-2-HYDROXY-1-BUTYL]THIO)ALKANOYL MOIETY AND THE CORRESPONDING SULFOXIDE AND SULFONE DERIVATIVES

This is a continuation of application Ser. No. 07/644,412, filed Jan. 22, 1991 and now abandoned.

BACKGROUND OF THE INVENTION

1. Field of the Invention

The present invention relates to novel compounds having the structural formula I:

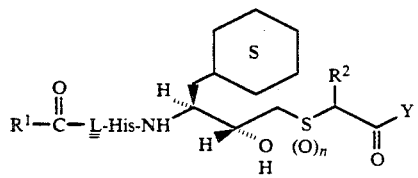

in which n is 0, 1 or 2,

is Boc-L-Phe; or a Boc-L-Phe surrogate such as

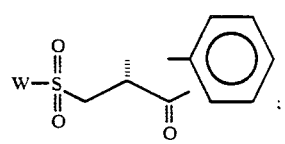

in which W is $(C_1-C_4alkyl)_3C-$ or $(C_1-C_4alkyl)_2CH-$; $R^2$ is alkyl; and Y is $OR^3$ or $NR^4R^5$ in which $R^3$ is hydrogen or alkyl and $R^4$ and $R^5$ are independently hydrogen, alkyl, aryl, heterocyclyl, aralkyl, heterocyclylalkyl, N-substituted aminoalkyl, N-substituted carbamoylalkyl, or $R^4$ and $R^5$ taken together with the nitrogen forming a 5 or 6 membered saturated or unsaturated ring.

These compounds exhibit renin inhibitory activity and are thus useful in the treatment of renin-associated hypertension and hyperaldosteronism.

The present invention is also concerned with pharmaceutical compositions containing the novel compounds of the present invention as active ingredients, with methods of treating renin-associated hypertension and hyperaldosteronism, with diagnostic methods which utilize the novel compounds of the present invention as well as methods of preparing the novel compounds of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or mainpulate renin-angiotensin system have met with success in the use of inhibitors of angiotensin I converting enzyme. In view of this success, it seems reasonable to conclude that a specific inhibitor of the limiting enzymatic step that ultimately regulates, angiotensin II production, the action of renin on its substrate, would be at least equally successful. Thus, an effective inhibitor of renin has been long sought as both a therapeutic agent and as an investigative tool.

2. Brief Description of the Prior Art

Renin inhibitors having the structural formula such as II, in which n=0 or 1,

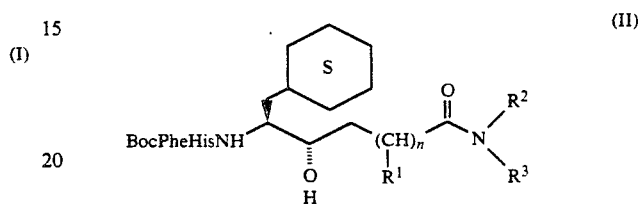

are known. See for example U.S. Pat. No. 4,650,661, EP 155,809, and EP 163,327. EP 236,734 discloses renin inhibitors in which "Boc Phe" is replaced by a surrogate containing a t-butyl sulfone group.

U.S. Pat. No. 4,609,641 discloses compounds of the type:

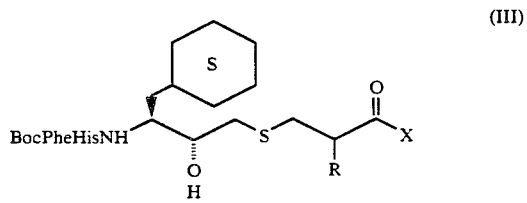

and

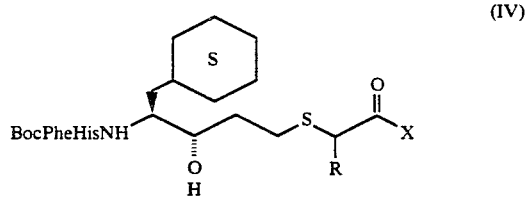

in which "X"=OR' or NR"R''' and R=H, alkyl etc. EP 172,347 discloses compounds of the type:

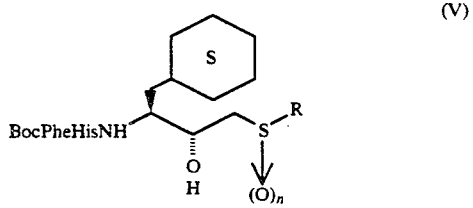

wherein n=0, 1, or 2 and R is alkyl, cycloalkyl, aryl or aralkyl. EP 184,855 discloses compounds of the type:

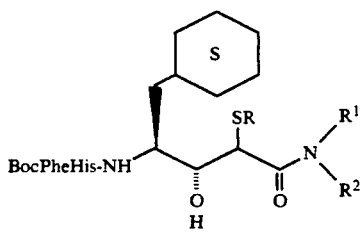

However, none of these references describe or suggest renin inhibitory compounds containing the moiety 2-[[(2R,3S)-3-amino-4-cyclohexyl-2-hydroxy-1-butyl]thio]alkanoyl and the sulfoxide and sulfone thereof of the formula VII.

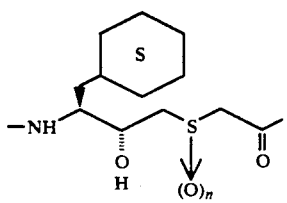

It is the presence of this moiety in the instant Compounds I which distinguishes over the prior art compounds described above.

For other articles describing previous efforts to devise renin inhibitors, see Marshall, *Federation Proc.* 35: 2494-2501, 1976; Burton et al., *Proc. Natl. Acad. Sci. USA* 77: 5476-5479, September 1980; Suketa et al., *Biochemistry* 14: 3188, 1975; Swales, *Pharmacol. Ther.* 7: 173-201, 1979; Kokubu et al., *J. Antibiotics* 28: 1016-1018, December 1975; Lazar et al., *Biochem. Pharmacol.* 23: 2776-2778, 1974; Miller et al., *Biochem. Pharmacol.* 21: 2941-2944, 1972; Haber, *Clinical Science* 59: 7s-19S, 1980; Rich et al., *J. Org. Chem.* 43: 3624, 1978, and *J. Med. Chem.* 23: 27, 1980; Burton et al., U.S. Pat. No. 4,269,827; Castro et al., U.S. Pat. No. 4,185,096; and Sankyo Jap. Pat. No. 76-067001.

DETAILED DESCRIPTION OF THE INVENTION AND PREFERRED EMBODIMENTS

In accordance with the present invention, there are provided renin inhibitory compounds of the formula I:

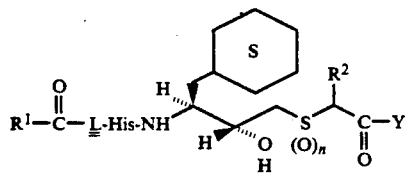

wherein n=0, 1 or 2;

is Boc-L-Phe or

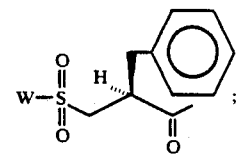

in which W is $(C_1-C_4 alkyl)_3 C—$ or $(C_1-C_4 alkyl)_2 CH—$; $R^2$ is $C_1$ to $C_6$ straight or branched-chain alkyl; Y is $OR^3$ or $NR^4 R^5$, in which $R^3$ is hydrogen or $C_1$ to $C_4$ alkyl; and $R^4$ and $R^5$ are independently selected from hydrogen, $C_1$ to $C_4$ alkyl, aryl, heterocyclyl, aralkyl, heterocyclylalkyl and N-substituted amino $C_1-C_6$ alkyl, in which the amino group may be part of a ring, which includes for example:

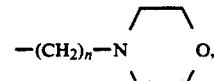

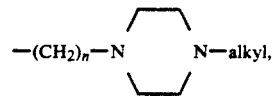

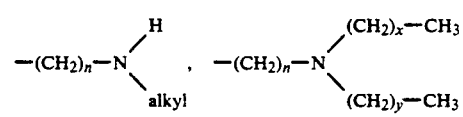

in which x and y may be equal or different and each is from 0 to 5 and n is from 1 to 6;

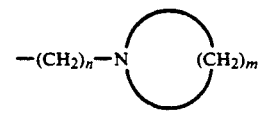

in which m is from 3 to 7, $—(CH_2)_n N^+ (CH_3)_3 Z^-$ in which Z is an anion such as a halide,

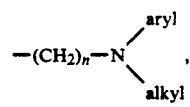

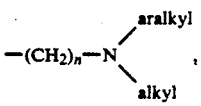

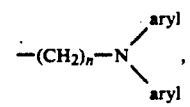

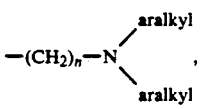

and the like, and N-substituted carbamoyl $C_1$ to $C_6$ alkyl which includes for example:

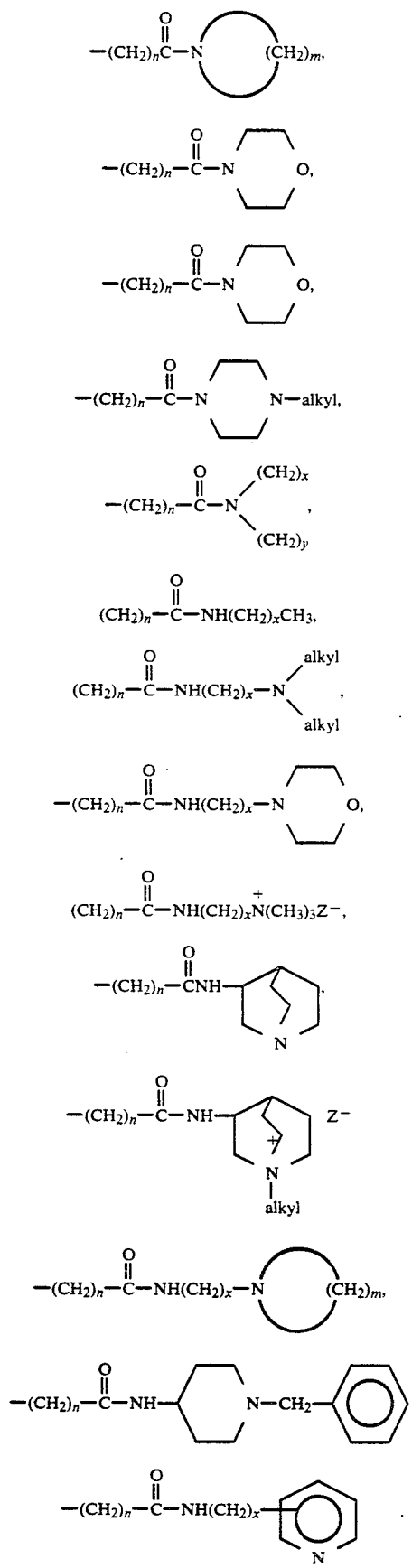

and the like, or $R^4$ and $R^5$ taken together with the nitrogen forming a 5 or 6 membered saturated or unsaturated ring. In the above, "alkyl," "aralkyl," n, x, y, z, and m have the same significance as defined.

As used herein and in the claims, aryl represents an aromatic ring of 6 to 10 carbon atoms e.g. phenyl and naphthyl and aralkyl represents aryl $C_1$-$C_4$ alkyl in which aryl is as defined.

The heterocyclic substituent recited above represents any 5- or 6-membered ring containing from one to four heteroatoms selected from the group consisting of nitrogen, oxygen, and sulfur; having various degrees of unsaturation; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Typical heterocyclic substituents include for example: piperidine, pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl. benzimidazolyl, benzothiazolyl, benzoxazolyl, furyl, thienyl, triazolyl, tetrazolyl and benzothienyl.

In the specification and in the claims the abbreviated designations have the following meaning: Boc means tert-butyloxycarbonyl, His means L-histidine, Phe means L-phenylalanine and "X" means [(2R,3S)-3-(Boc-L-phenylalanyl-L-histidylamino)-4-cyclohexyl-2-hydroxy-1-butyl].

The Formula I compounds where there is an acidic or basic group can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D glucamine, and salts with amino acids such as arginine, lysine, and so forth. Also, the basic nitrogen containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dipersible products are thereby obtained.

The present invention is also directed to combinations of the novel Formula I compounds with one or more antihypertensive agents selected from the group consisting of diuretics, α and/or β-adrenergic blocking agents, CNS-acting agents, adrenergic neuron blocking agents, vasodilators, angiotensin I converting enzyme inhibitors, and other antihypertensive agents.

For example, the compounds of this invention can be given in combination with such compounds or salt or other derivative forms thereof as:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate, sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; meteoprolol; nadolol; propranolol; timolol;

((±)-2-[3-(tert-butylamino)-2-hydroxypropoxy]-2-furan-anilide)(ancarolol);

(2-acetyl-7-(2-hydroxy-3-isopropylaminopropoxy) benzofuran HCl)(benfunolol);

((±)-1-(isopropylamino)-3-(p-(2-cyclopropylmethoxyethyl)-phenoxy)-2-propranol HCl) (betaxolol);

(1-[(3,4-dimethoxyphenethyl)amino]-3-(m-tolyloxy)-2-propanol HCl)(bevantolol);

((±)-1-(4-((2-isopropoxyethoxy)methyl)phenoxy)-3-isopropylamino-2-propanol)fumarate)(bisoprolol); .

(4-(2-hydroxy-3-[4-phenoxymethyl) piperidino]propoxy)-indole);

(carbazolyl-4-oxy-5,2-(2-methoxyphenoxy)-ethylamino-2-propanol);

(1-((1,1-dimethylethyl)amino)-3-((2-methyl-1H-indol-4-yl)oxy)-2-propanol benzoate)(bopindolol);

(1-(2-exobicyclo[2 2.1]-hept-2-ylphenoxy)-3-[(1-methylethyl)-amino]-2 propranol HCl)(bornaprolol);

(o-[2-hydroxy-3-[(2-indol-3-yl-1,1-dimethylethyl-) amino]propoxy]benzonitrile HCl)(bucindolol);

(α-[(tert.butylamino)methyl]-7-ethyl-2-benzofuranmethanol)(bufuralol);

(3-3-acetyl-4-[3-(tert.butylamino)-2-hydroxypropyl]-phenyl]-1,1-diethylurea HCl)(celiprolol);

((±)-2-[2-[3-[(1,1-dimethylethyl)amino]-2-hydroxypropoxy]phenoxy]-N-methylacetamide HCl) (cetamolol);

(2-benzimidiazolyl-phenyl(2-isopropylaminopropanol));

((±)-3′-acetyl-4′-(2-hydroxy-3-isopropylaminopropoxy)acetanilide HCl)(diacetolol);

(methyl-4-[2-hydroxy-3-[(1-methylethyl)aminopropoxy]]-benzenepropanoate HCl)(esmolol);

(erythro-DL-1-(7-methylindan-4-yloxy)-3-isopropylaminobutan-2-ol);

1-(tert.butylamino)-3-[o-(6-hydrazino-3-pyridazinyl)-phenoxy]-2-propanol diHCl)(prizidilol);

((−)-2-hydroxy-5-[(R)-1-hydroxy-2-[(R)-(1-methyl-3-phenylpropyl)amino]ethyl]benzamide);

(4-hydroxy-9-[2-hydroxy-3-(isopropylamino)-propoxy]-7-methyl-5H-furo[3,2-g][1]benzopyran-5-one) (iprocrolol);

(4-[3-(tert.butylamino)-2-hydroxypropoxy]-N-methyl isocarbostyril HCl);

((±)-N-2-[4-(2hydroxy-3-isopropylaminopropoxy)-phenyl]ethyl-N′-isopropylurea)(pafenolol);

(3-[[(2-trifluoroacetamido)ethyl]amino]-1-phenoxypropan-2-ol);

(N-(3-(o-chlorophenoxy)-2-hydroxypropyl)-N′-(4′-chloro-2,3-dihydro-3-oxo-5-pyridazinyl)ethylene diamine);

((±)-N-[3-acetyl-4-[2-hydroxy-3-[(1-methylethyl)amino]propoxy]phenyl]butanamide)(acebutolol);

(7-[3-[[2-hydroxy-3-[(2-methylindol-4-yl)oxy]-propyl]amino]butyl]thiophylline)(teoprolol);

((±)-1-tert.butylamino-3-(thiochroman-8-yloxy)-2-propanol)(tertatolol);

((±)-1-tert.butylamino-3-(2,3-xylyloxy)-2-propanol HCl)(xibenolol);

(8 -[3-(tert.butylamino)-2-hydroxypropoxy]-5-methyl-coumarin)(bucumolol);

(2-(3-(tert.butylamino)-2-hydroxy-propoxy)benzonitrile HCl)(bunitrolol);

((±)-2′-[tert.butylamino)-2-hydroxypropoxy-5′-fluorobutyrophenone])(butofilolol);

(1-(carbazol-4-yloxy)-3-(isopropylamino)-2-propanol)-(carazolol);

(5-(3-tert.butylamino-2-hydroxy)propoxy-3,4-dihydrocarbostyril HCl)(carteolol);

(1-(tert.butylamino)-3-(2-5-dichlorophenoxy)-2-propanol)(cloranolol);

(1-(inden-4(or 7)-yloxy)-3-(isopropylamino)-2-propanol HCl)(indenolol);

(1-isopropylamino-3-[(2-methylindol-4-yl)oxy]-2-propanol)(mepindol);

(1-(4-acetoxy-2,3,5-trimethylphenoxy)-3-isopropylaminopropan-2-ol)(metipranolol);

(1-(isopropylamino)-3-(o-methoxyphenoxy)-3[(1-methylethyl)amino]-2-propanol)(moprolol);

((1-tert.butylamino-3-[(5,6,7,8-tertrahydro-cis-6,7,-dihydroxy-1-napthyl)oxy]-2-propanol)(nadolol);

((S)-1-(2-cyclopentylphenoxy)-3-[(1,1-dimethylethyl)amino]2-propanol sulfate (2:1)) (penbutolol);

(4′-[1-hydroxy-2-(amino)ethyl]methanesulfonanilide)(sotalol);

(2-methyl-3-[4-(2-hydroxy-3-tert.butylaminopropoxy)-phenyl]-7-methoxy-isoquinolin-1-(2H one);

1-(4-(2-(4-flurophenyloxy)ethoxy)phenoxy-3-isopropylamino-2-propanol HCl);

((−)-p-[3-[(3,4-dimethoxyphenethyl)amino]-2-hydroxyprop-oxy]-8-methylcinnamonitrile) (pacrinolol);

((±)-2-(3′-tert.butylamino-2′-hydroxypropylthio)-4-(5′carbamoyl-2′-thienyl)thiazole HCl) (arotinolol);

((±)-1-[p-[2-cyclopropylmethoxy)ethoxy]phenoxy]-3-(isopropylamino)-2-propanol)(cicloprolol);

((±)-1-[3-chloro-2-methylindol-4-yl)oxy]-3-[(2-phenoxyethyl)amino}-2-propanol)(indopanolol);

((±)-6-[[2-[[3-(p-butoxyphenoxy)-2-hydroxypropyl]-amino]ethyl]amino]-1,3-dimethyluracil)(pirepolol);

(4-(cyclohexylamino)-1-(1-naphtholenyloxy)-2-butanol);

(1-phenyl-3-[2-[3-(2-cyanophenoxy)-2-hydroxypropyl]aminoethyl]hydantoin HCl);

(3,4-dihydro-8-(2-hydroxy-3-isopropylaminopropoxy)-3-nitroxy-2H-1-benzopyran)(nipradolol);

α and β-Adrenergic Blocking Agents:

((±)-1-tert.butylamino)-3-[o-[2-(3-methyl-5-isoxazolyl)-vinyl]phenoxy]-2-propanol)(isoxaprolol);

(1-isopropylamino-3-(4-(2-nitroxyethoxy)phenoxy)-2-propanol HCl);

(4-hydroxy-α-[[3-(4-methoxyphenyl)-1-methylpropyl]-aminomethyl]-3-(methylsulfinyl)-benzmethanol HCl)(sulfinalol);

(5-[1-hydroxy-2-[[2-(o-methoxyphenoxy)ethyl]amino]ethyl]-2-methylbenzenesulfonamide HCl);

(5-[1-hydroxy-2-[(1-methyl-3-phenylpropyl)amino]ethyl]-salicylamide HCl)(labetalol);

(1-((3-chloro-2-methyl-1H-indol-4-yl)oxy-3-((2-phenoxyethyl)amino)-2-propanol hydrogenmalonate) (ifendolol);

(4-(2-hydroxy-3-[(1-methyl-3-phenylpropyl)amino]propoxy)benezenacetamide);

(1-[3-[[3-(1-naphthoxy)-2-hydroxypropyl]-amino]-3,3-dimethylpropyl]-2-benzimidazolinone);

(3-(1-(2-hydroxy-2-(4-chlorophenylethyl)-4-piperidyl)-3,4-dihydroxy)quinoxoline-2(1H) one);

CNS-Acting Agents: clonidine; methyldopa;

Adrenergic Neuron Blocking Agents: guanethidine; reserpine and other rauwolfia alkaloids such as rescinnamine;

Vasodilators: diazoxide; hydralazine; minoxidil;

Angiotensin I Converting Enzyme Inhibitors:

1-(3-mercapto-2-methyl-1-oxopropyl)-L-proline (captopril);

(1-(4-ethoxycarbonyl-2,4(R,R)-dimethylbutanoyl)-indoline-2(S)-carboxylic acid);

(2-[2-[[1-(ethoxycarbonyl)-3-phenylpropyl]amino]-1-oxopropyl]-1,2,3,4-tetrahydro-3-isoquinoline carboxylic acid);

((S)-1-[2-[[1-(ethoxycarbonyl)-3-phenylpropyl]amino]-1-oxopropyl]octahydro-1H-indole-2-carboxylic acid HCl);

(N-cyclopentyl-N-(3-(2,2-dimethyl-1-oxopropyl) thiol-2-methyl-1-oxopropyl)glycine)(pivalopril);

((2R,4R)-2-(2-hydroxyphenyl)-3-(3-mercaptopropionyl)-4-thiazolidinecarboxylic acid;

(1-(N-[1(S)-ethoxycarbonyl-3-phenylproppyl]-(S)-alanyl)-cis,syn-octahydronindol-2(S)-carboxylic acid HCl);

((−)-(S)-1-[(S)-3-mercapto-2-methyl-1-oxopropyl]-indoline-2-carboxylic acid;

([1(S),4S]-1-[3-benzoylthio)-2-methyl-1-oxopropyl]-4-phenylthio-L-proline;

(3-([1-ethoxycarbonyl-3phenyl-(1S)-propyl]amino)-2,3,4,5-tetrahydro-2-oxo-1(3S)-benzazepine-1-acetic acid HCl);

(N-(2-benzyl-3-mercaptopropanoyl)-S-ethyl-L-cysteine) and the S-methyl analogue;

(N-(1(S)-ethoxycarbonyl-3-phenylpropyl)-L-alanyl-Lproline maleate)(enalapril);

N-[1-(S)-carboxy-3-phenylpropyl]-L-alanyl-1-proline;

$N^2$-[1-(S)-carboxy-3-phenylpropyl]-L-lysyl-L-proline(-lysinopril);

Other Antihypertensive Agents: aminophylline; cryptenamine acetates and tannates; deserpidine; meremethoxylline procaine, pargyline; trimethaphan camsylate; and the like, as well as admixture and combinations thereof.

Typically, the individual daily dosages for these combinations can range from about one-fifth of the minimally recommended clinical dosages to the maximum recommended levels for the entities when they are given singly. Coadministration is most readily accomplished by combining the active ingredients into a suitable unit dosage form containing the proper dosages of each. Other methods of coadministration are, of course, possible.

The novel compounds of the present invention possess an excellent degree of activity in treating renin-associated hypertension and hyperaldostemoism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may e formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irrating excipient which is solid at ordinary temperatures but liquid at the rectal temperature and will therefore melt in the rectum to release the drug. Such materials are cocoa butter and polyethylene glycols.

Dosage levels of the order of 0.1 to 4.0 grams per day are useful in the treatment of the above indicated conditions. For example, renin-associated hypertension and hyperaldosteronism are effectively treated by the administration of from 1.0 to 50 milligrams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a compound according to formula I.

Also included within the scope of the present invention is a method of treating renin-associated hypertensin and hyperaldosteonism. Comprising administering to a patient in need of such treatment, a therapeutically effective amount of a compound I or a pharmaceutically acceptable salt thereof in a pharmaceutical carrier.

Compound (I) may also be utilized in diagnostic methods for the purpose of establishing the significance of renin as a causative or contributory factor in hypertension or hyperaldosteronism in a particular patient. For this purpose the compound of the present invention may be administered in a single dose of from 0.1. to 10 mg per kg of body weight.

Both in vivo and in vitro methods may be employed. In the in vivo method, a compound of the present invention is administered to a patient, preferably by intravenous injection, although parenteral administration is also suitable, at a hypotensive dosage level and as as single dose, and there may result a transitory fall in blood pressure. This fall in blood pressure, if it occurs, indicates supranormal plasma renin levels.

An in vitro method which may be employed involves incubating a body fluid, preferably plasma, with a compound of the present invention and, after deproteinization, measuring the amount of angiotensin II produced in nephrectomized, pentolinium-treated rats. Another in vitro method involves mixing the plasma or other body fluid with a compound of the present invention and injecting the mixture into a test animal. The difference in pressor response with and without added peptide is a measure of the renin content of the plasma.

According to the present invention, Compound I is prepared via addition of a 2-mercaptoalkanoyl derivative to the chiral epoxide of the formula:

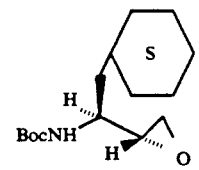

The above compound in turn is prepared in high optical and diastereomeric purity by addition of dimethyloxosulfonium methylide to the chiral Boc-amino aldehyde.

More particularly, the compounds of the present invention are prepared in accordance with the following reaction scheme:

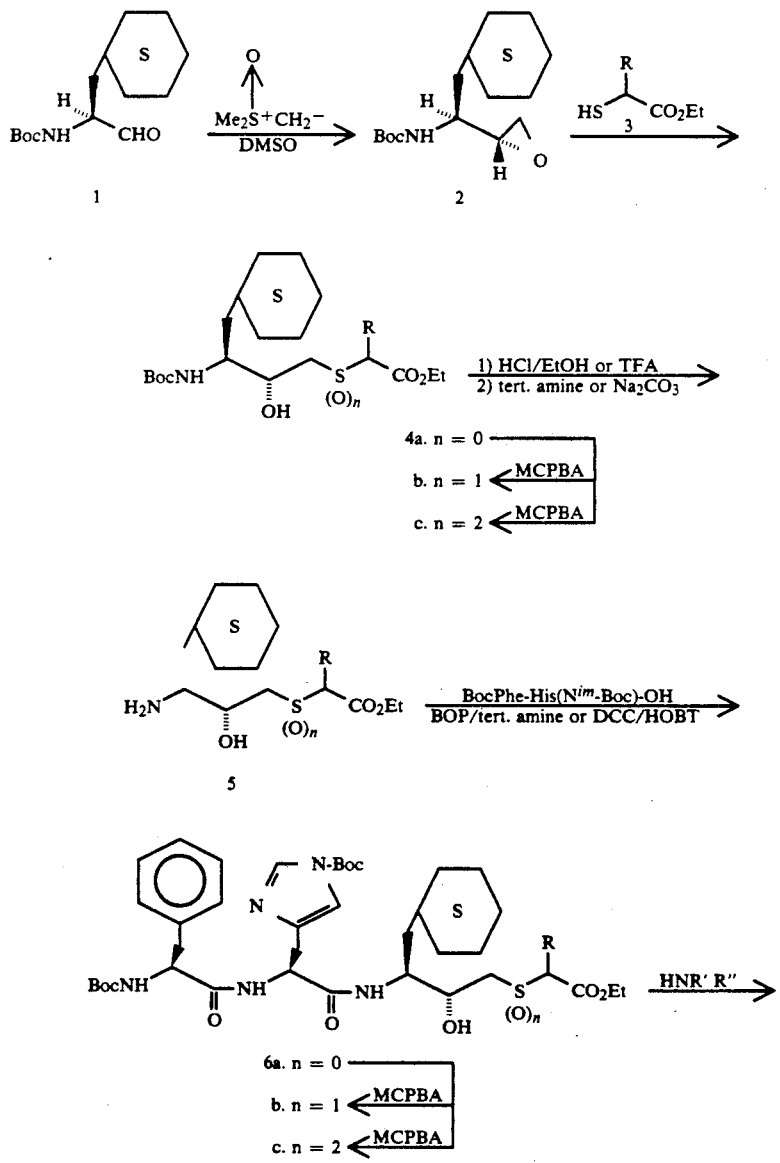

-continued
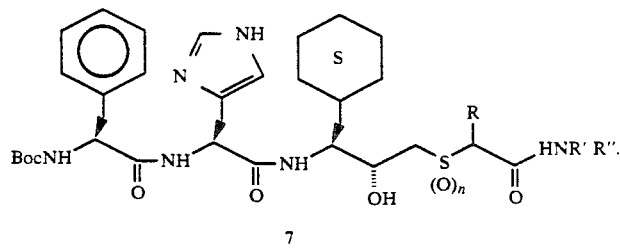
7
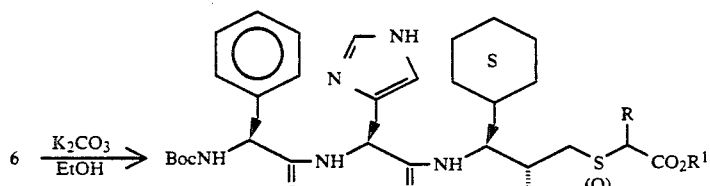
6 →(K₂CO₃ / EtOH)
8. R' = H and
9. R' = Et
or 6 (R = alkyl) →(H₂NNH₂ / 20°) 9;
or 8 →(HNR'R" / BOP, Et₃N) 7;
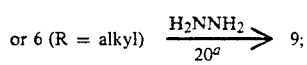
HNR'R" →
10
1) HCl/MeOH or TFA
2) tert. amine or Na₂CO₃
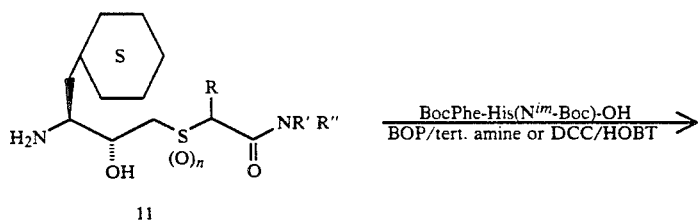
11
BocPhe-His(N^im-Boc)-OH / BOP/tert. amine or DCC/HOBT →
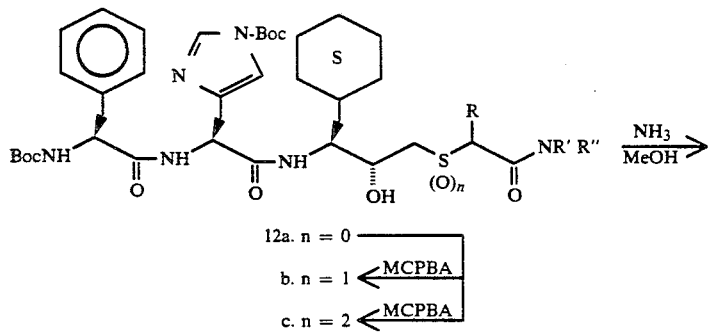
12a. n = 0
 b. n = 1 ←MCPBA
 c. n = 2 ←MCPBA
NH₃ / MeOH →

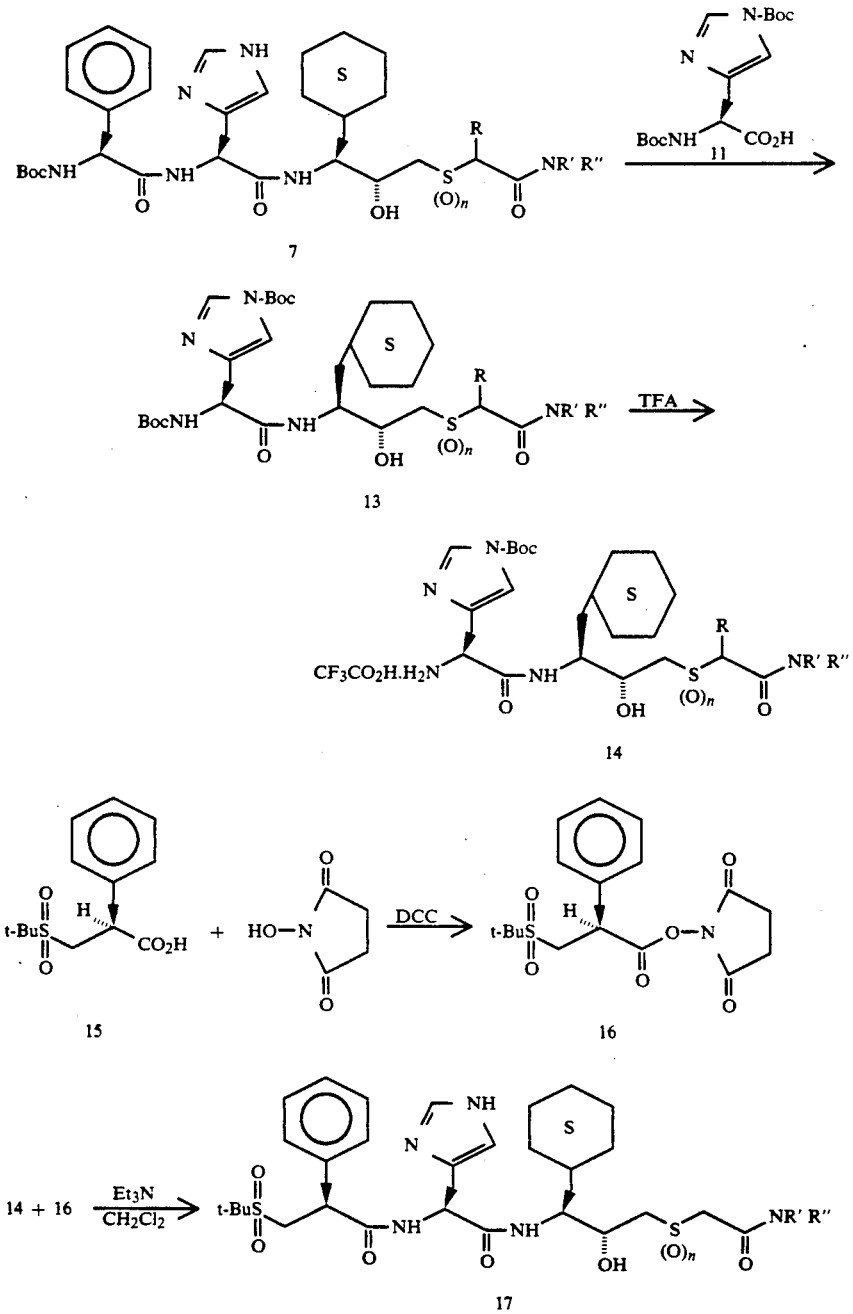

Referring to the foregoing reaction scheme, the synthesis of chiral epoxide 2 is fully described in our co-pending application (Case 17775) Ser. No. 231,320 filed on Aug. 12, 1988. This is incorporated herein by reference.

Addition of the α-mercapto ester 3 to the epoxide yields the optically active adduct 4a. The addition may be accomplished by reacting approximately equimolar quantities of 2 and 3 in the presence of 1 equivalent of a tertiary amine such as triethylamine. The reaction is run at 20° to 50° C. (preferably at room temperature) in a compatible solvent (such as ethanol, acetonitrile, tetrahydrofuran, or methylene chloride) and is usually complete within 24 hours. The α-mercapto esters are either commercially available (for R=H) or may be prepared in optically active form from the corresponding α-amino acid of opposite configuration by known methods, e.g. J. A. Yankeelov and K. F. Fok, UK Patent Appl. GB 2,013,210 (1979); J. Feder and H. I. Weingarten, European Patent Appl. EP 149,593 (1985); N. Acton and A. Komoriya, *Org. Prep. Proced. Int.*, 14, 381 (1982), and a final acid-catalyzed esterification step, see C. R. Noe, *Chem. Ber.*, 115, 1607 (1982).

The Boc protecting group of 4 is removed by treatment with anhydrous HCl (preferably, saturated HCl in ethanol—for the ethyl ester—at room temperature) or, alternatively, with trifluoroacetic acid (neat or diluted with methylene chloride) at room temperature. Following evaporative removal of solvent and excess acid, the free amine 5 may be generated in situ in the next step by addition of an equivalent of a tertiary amine (e.g., triethylamine) or isolated by partitioning the amine salt between an organic solvent (e.g., ethyl acetate) and saturated aqueous sodium carbonate solution, then concentrating the organic phase.

The amine 5 is coupled with Boc-L-phenylalanyl-N$^{im}$-Boc-L-histidine using standard peptide coupling conditions designed to minimize racemization. Preferred coupling reagents include benzotriazol-1-yloxytris (dimethylamino)phosphonium hexafluorophosphate ("BOP Reagent") (in the presence of a tertiary amine) or N,N'-dicyclohexylcarbodiimide (DCC)/1-hydroxybenzotriazole (HOBT) in a compatible solvent such as methylene chloride or acetonitrile. Treatment of the resulting product 6 with a suitably reactive amine (e.g., a primary aliphatic amine or unhindered secondary amine) leads to formation of the amide 7 with simultaneous removal of the N$^{im}$-Boc group from histidine. The amine itself may be used as solvent, or alternatively, the amine (4 to 10 equivalents) is diluted with a solvent (preferably ethanol), and the reaction is carried out at 20°–100° C. for 1 to 4 days.

The sulfoxide and sulfone analogs are obtained by peracid oxidation of the thioethers, preferably at the stage of either intermediate 4 or intermediate 6. The thioether may be treated at room temperature with 1.0 to 1.2 equivalents of m-chloroperoxybenzoic acid (MCPBA) in a solvent such as methylene chloride or glacial acetic acid to obtain the sulfoxide. The sulfone is obtained similarly from the thioether except that 2.5 to 5 (preferably 3 to 4) equivalents of MCPBA are used.

Treatment of 6 with approximately 5 to 6 equivalents of pulverized anhydrous potassium carbonate in ethanol at room temperature for 1 to 6 hours leads to a mixture of imidazole deblocked ester 9 and the corresponding acid 8, which are readily separated. For bulky R groups, the ester group in 6 is sufficiently unreactive that 9 may be obtained from 6 by treatment with hydrazine hydrate (several equivalents) in ethanol for about 1 hour. In the case of compounds derived from optically active α-mercapto esters (3), this latter method allows removal of the N$^{im}$-Boc group from 6 without epimerization of the R substituent.

The acid 8 may be coupled with an amine using standard peptide coupling conditions (preferably using "BOP reagent" in the presence of triethylamine in methylene chloride) to yield 7. This method is particularly preferred for amines which are not sufficiently reactive to form an amide directly from the ester 6 or in cases where it is not feasible to use the amine in large excess.

In an alternative route to 7, the amide is formed at an earlier stage by direct reaction of the ester intermediate 4 with an amine under the conditions described above for the synthesis of 7 from 6. The product 10 is deprotected either with anhydrous HCl (preferably saturated HCl in methanol) or with anhydrous trifluoroacetic acid, as in the preparation of 5 from 4. Coupling of the amine 11 with Boc-L-phenylalanyl-N$^{im}$-Boc-L-histidine under conditions described above for the synthesis of 6 yields 12. Oxidation of 12a to the sulfoxide 12b or sulfone 12c may be carried out with MCPBA using the conditions described above. Removal of the N$^{im}$-Boc group from 12 is accomplished by treatment with saturated methanolic ammonia for 2 to 6 hours, yielding 7.

The amine 11 may also be coupled with N$^\alpha$,N$^{im}$-diBoc-L-histidine (preferably using "BOP reagent" plus triethylamine in methylene chloride) to give 13. This material is deblocked with anhydrous trifluoroacetic acid to give amine 14 as a trifluoroacetate salt, used without purification. Intermediate 14 may then be coupled with a replacement for Boc-L-phenylalamine. Thus, 14 is coupled with the chiral t-butyl sulfone-containing acid 15 [P. Buhlmayer et al. *J. Med. Chem.*, 31, 1839 (1988)] via the pre-formed N-hydroxysuccinimide ester 16. Reaction of 14 and 16 in the presence of triethylamine in methylene chloride at room temperature yields 17.

Some of the compounds which fall within the scope of I along with inhibition data (IC$_{50}$) in the plasma renin assay follow.

Briefly, the assay described by J. A. Millar et al., in Clinica Chimica Acta (1980) 101, 5–15 and K. Poulsen and J. Jorgensen in J. Clin Endocrinol. Metab. (1974) 39, 816.

It is based on the measurement, by radioimmunoassay, of Angiotensin-I released from human renin substrate by human renin in human plasma. The inhibitor is dissolved in 0.01N HCl (10 μl) and added to human plasma (75 μl) containing EDTA, and angiotensin-I antibody (15 ml) in 3M-Tris.HCl buffer (pH 6.9).

After incubation at 37° C. for 0–120 minutes, the enzymic reaction is quenched by the addition of ice cold 0.25M Tris/HCl buffer (pH 7.4) containing 0.01% of bovine serum albumin. $^{125}$I-labelled angiotensin-I is added, followed by equilibration at 4° C. for 48 hours. Free and bound ligand are separated by the addition of dextran-coated charcoal, and the amount of bound radio-ligand determined in a gamma counter.

The results for the renin inhibitory activities of the present compounds thus tested are expressed as the IC$_{50}$ (the molar concentration required to cause 50% inhibition). They are as follows:

| | |
|---|---|
| 2-[X-thio]acetic acid | (904 nM) |
| ethyl 2-[X-thio]acetate | (58 nM) |
| 4-[[2-[X-thio]acetamido]methyl]pyridine | (92 nM) |
| 4-[2-[2-[X-thio]acetamido]ethyl]morpholine | (40 nM) |
| N-[2-[X-thio]acetyl]-N,N'-dimethylethylenediamine | (161 nM) |
| 4-[2-[X-thio]acetyl]-1-methylpiperazine | (29 nM) |
| 3-[2-[X-thio]acetamido]quinuclidine | (29 nM) |
| ethyl (2S)-2-[X-thio]-4-methylpentanoate | (305 nM) |
| ethyl (2R)-2-[X-thio]-4-methylpentanoate | (288 nM) |
| 4-[2-[[(2 RS )-2-[X-thio]-4-methylpentanoyl]-amino]ethyl]morpholine | (73 nM) |
| 4-[2-[2-[X-sulfinyl]acetamido]ethyl]morpholine | (19 nM) |
| 4-[2-[2-[X sulfonyl]acetamido]ethyl]morpholine | (9.4 nM) |
| 4-[2-[X-sulfonyl]acetyl]-1-methylpiperazine | (20 nM) |
| 1-benzyl-4-[2-[X-sulfonyl]acetamido]piperidine | (34 nM) |
| 3-[2-[X-sulfonyl]acetamido]quinuclidine-N-oxide | (4.2 nM) |
| 4-[2-[[(2 RS )-2-[X-sulfinyl]-4-methyl-pentanoyl]amino]ethyl]morpholine | (88 nM) |
| 4-[2-[[2 RS )-2 [X-sulfonyl]-4-methyl-pentanoyl]amino]ethyl]morpholine | (77 nM) |
| 4-[2-[2-[[(2R,3S)-3-[N$^\alpha$-[(S)-2-[(t-butylsulfonyl)-methyl]-3-phenylpropionyl]-L-histidylamino]-4-cyclohexyl-2-hydroxy-1-butyl]sulfonyl]-acetamido]ethyl]morpholine | (7.2 nM) |

In the above compounds X means [(2R,3S)-3-(Boc-L-phenylalanyl-L-histidylamino)-4-cyclohexyl-2-hydroxy-1-butyl].

Preparation of the compounds of the present invention is illustrated in the following examples:

EXAMPLE 1

(2R,3S)-3-(t-Butoxycarbonylamino)-4-cyclohexyl-1,2-epoxybutane.

In an oven-dried 250 ml 3-necked round-bottomed flask was placed 1.58 g (39.5 mmole) of sodium hydride (60% in oil). To remove the oil, the sodium hydride was washed with petroleum ether (removed by decantation). The flask was immediately flushed with $N_2$, and 50 ml of dry DMSO was introduced through a septum. The mixture was stirred at room temperature under $N_2$ as 8.32 g (38.6 mmole) of trimethyloxosulfonium methylide was added over a period of 5 minutes via a solid addition funnel. Within 20 minutes, $H_2$ evolution had ceased, and a nearly clear solution was obtained. A solution of 8.2 g (32.1 mmole) of N-Boc-3-cyclohexyl-L-alaninal [J. Boger, et al., *J Med. Chem.*, 28, 1779 (1985)] in 50 ml of dry THF was added over 8 minutes from a dropping funnel. The mixture became cloudy, and precipitation occurred. After 1 hour, the mixture was concentrated in vacuo to remove the THF. The residual DMSO solution was partitioned between 200 ml of ether and 200 ml of $H_2O$. The aqueous phase was extracted with a further 200 ml of ether. The combined ether extracts were washed with 300 ml of $H_2O$, then dried ($Na_2SO_4$), filtered, and concentrated in vacuo. The residual oil was taken up in hexane and applied to a column of silica gel (65×4.4 cm) packed in hexane. The column was eluted with 4:1 hexane-ether, and fractions were evaluated by TLC in this system (visualized by $I_2$ vapor). [NOTE: The desired "threo" epoxide runs slightly ahead of the "erythro" epoxide on TLC. The NMR correlations described in B. E. Evans, et al., *J. Org. Chem.*, 50, 4615 (1985) were used to establish the relative configurations of the diastereomeric epoxide products.] Fractions containing exclusively the "threo" epoxide (eluted ahead of the minor "erythro" product) were combined and concentrated to yield 4.07 g of waxy semi-solid having characteristic NMR peaks in $CDCl_3$ at δ 2.60, 2.73, 2.98, 4.01 and 4.30 (vs. 2.75, 2.84, 3.55 and 4.37 for the "erythro" diastereomer). At this stage the epoxide is diastereomerically pure but not optically pure. Optical purity can be achieved by selectively crystallizing out the undesired 2S,3R isomer (as the racemate) at low temperature. Thus, 1.14 g of the above epoxide, $[\alpha]^{20}_D$ −5.9° (c 2, $CHCl_3$), was dissolved in 10 ml of petroleum ether, placed in an acetone bath, and kept under $N_2$ as the bath temperature was gradually lowered by addition of dry ice. When the bath temperature reached approximately −30° C., crystallization began spontaneously. The bath was maintained at −20° to 30° C. for several minutes. When it appeared that no further crystallization was occurring, the mixture was rapidly filtered under $N_2$ to give (after drying) 0.40 g of white crystals, mp 58°-59.5° C. $[\alpha]^{20}_D$ −1.8° (c 2, $CHCl_3$). Concentration of the mother liquor yielded 615 mg (25% overall) of colorless, viscous residual oil, $[\alpha]^{20}_D$ −11.5° (c 2, $CHCl_3$). In subsequent runs, the crystallization was carried out at −40° to 60° C., giving residual oily epoxide with $[\alpha]^{20}_D$'s (c 2, $CHCl_3$) of −12.8° to 13.1° (c 2, $CHCl_3$). Rotations of this magnitude are indicative of high optical purity for the 2R,3S epoxide, and petroleum ether solutions of this purified material do not deposit additional crystals of racemate, even when seeded and cooled to −78° C.

EXAMPLE 2

Ethyl 2-[[2R,3S)-3-(t-Butoxycarbonylamino)-4-cyclohexyl-2-hydroxy-1-butyl]thio]acetate A solution of 1.41 g (5.25 mmole) of (2R,3S)- 3-(t-butoxycarbonylamino)-4-cyclohexyl-1,2-epoxybutane, 0.55 ml (0.60 g, 5 mmole) of ethyl 2-mercaptoacetate, and 0.70 ml (0.51 g, 5 mmole) of triethylamine in 15 ml of absolute ethanol was stirred overnight at room temperature under a nitrogen atmosphere. The resulting solution was rotary evaporated in vacuo (oil pump) at room temperature. The viscous, golden-yellow residual oil was chromatographed on a column of silica gel 60 (60×3.5 cm) packed in hexane (elution with 7:1 and then 4:1 hexane-ethyl acetate). Concentration of the clean product fractions yielded 1.64 g (84%) of colorless, viscous oil, $[\alpha]^{20}_D$ −43.8° (c 2, $CHCl_3$), virtually homogeneous by TLC (4:1 hexane-ethyl acetate). The structure was confirmed by 200 MHz NMR and mass spectrum.

Analysis ($C_{19}H_{35}NO_5S$)

Calcd: C, 58.58; H, 9.06; N, 3.60; Found: C, 58.71; H, 9.07; N, 3.57

EXAMPLE 3

Ethyl 2-[[(2R,3S)-3-(Boc-L-phenylalanyl-$N^{im}$-Boc-L-histidyl-amino)-4-cyclohexyl-2-hydroxy-1-butyl]thio]acetate To 1.56 g (4 mmole) of ethyl 2-[[(2R,3S)-3-(t-butoxycarbonylamino)-4-cyclohexyl-2-hydroxy-1-butyl]thio]acetate was added 15 ml of absolute ethanol, freshly saturated with HCl gas at room temperature. The resulting solution was stirred under a drying tube. Gas evolution, initially vigorous, subsided within a few minutes. After about 1 hour the solution was evaporated in a stream of $N_2$ while being stirred at 40° C. The residue was dried in vacuo (oil pump, KOH trap), then dissolved in 20 ml of dry $CH_2Cl_2$ and treated with 1.11 ml (808 mg, 8 mmole) of triethylamine. The solution was re-concentrated and again dried in vacuo (oil pump) with only slight warming. The residual gum was treated successively with 1.89 g (4 mmole) of Boc-L-phenylalanyl-$N^{im}$-Boc-L-histidine, 1.77 g (4 mmole) of benzotriazol-1-yloxy-tris(dimethylamino)phosphonium hexafluorophosphate ("BOP Reagent"), 25 ml of dry $CH_2Cl_2$, and 0.56 ml (404 mg, 4 mmole) of triethylamine. The resulting solution was stirred under $N_2$ at room temperature for 17 hours and then concentrated in vacuo at room temperature. The residual oil was dissolved in ethyl acetate (125 ml), filtered, and washed successively with 1×25 ml of $H_2O$, 3×25 ml of saturated aqueous $NaHCO_3$ solution, and finally 1×25 ml of saturated NaCl solution. Concentration of the organic phase (dried over $MgSO_4$) gave an oil which was chromatographed on a column of silica gel 60 (64×3.5 cm; elution with 99:1 and then 98:2 $CHCl_3$-isopropanol). Concentration of the product fractions yielded 1.45 g (47%) of a colorless glass, homogeneous by TLC (97:3 $CHCl_3$-isopropanol). The structure was verified by 200 MHz NMR ($CDCl_3$) and mass spectrum.

Analysis ($C_{39}H_{59}N_5O_9S \cdot 0.5H_2O$)

Calcd: C, 59.82; H, 7.72, N, 8.95; Found: C, 60.07; H, 7.87, N, 8.67

EXAMPLE 4

2-[[(2R,3S)-3-(Boc-L-phenylalanyl-L-histidylamino)-4-cyclohexyl-2-hydroxy-1-butyl]thio]acetic acid and its ethyl ester.

A mixture of 1.39 g (1.8 mmole) of ethyl 2-[[(2R,3S) 3-(Boc-L-phenylalanyl-$N^{im}$-Boc-L-histidylamino)-4-cyclohexyl-2-hydroxy-1-butyl]thio]acetate. 1.38 g (10 mmole) of pulverized anhydrous $K_2CO_3$, and 70 ml of absolute ethanol was stirred vigorously at room temperature for 3 hours and then concentrated in vacuo (oil pump) at $\leq 20°$ C. The residue was treated with 100 ml of ethyl acetate, and the mixture was stirred vigorously for 15 minutes. The filtered ethyl acetate solution was shaken with 20 ml of $H_2O$. The gelatinous aqueous layer was separated and acidified with glacial acetic acid, giving a voluminous precipitate, which was collected on a filter and washed with $H_2O$. Drying in vacuo at 60° C. in the presence of $P_2O_5$ afforded 622 mg of 2-[[(2R,3S) 3-(Boc-L-phenylalanyl-L-histidylamino)-4-cyclohexyl-2-hydroxy-1-butyl]thio]acetic acid as a white powder, mp 178°–179° C. dec. (preliminary softening), TLC virtually homogeneous in 80:20:2 $CHCl_3$—MeOH $H_2O$ containing a small amount added acetic acid. Mass spectrum and 200 MHz NMR (DMSO-$d_6$) confirmed the structure.

Analysis ($C_{32}H_{47}N_5O_7S.0.25H_2O$)

Calcd: C, 59.10; H, 7.36; N, 10.77; Found: C, 58.90; H, 7.26; N, 10.77

The ethyl acetate phase from the above separation was washed further with $2 \times 20$ ml of $H_2O$, then dried over $Na_2SO_4$, filtered, and concentrated in vacuo. The glassy residue was chromatographed on a column of silica gel 60 ($48 \times 2.4$ cm). The column was eluted with 97:3 $CH_2Cl_2$—MeOH until a nonpeptidyl by-product had been removed and then with 96:4 $CH_2Cl_2$—MeOH. Concentration of the product fractions and trituration of the residue with ether yielded 265 mg of ethyl 2-[[(2R,3S) 3-(Boc-L-phenylalanyl-L-histidylamino)-4-cyclohexyl-2-hydroxy-1-butyl]thio]acetate as a white powder, mp 97°–99° C., TLC homogeneous in 9:1 $CHCl_3$—MeOH. From the supernatant was recovered a usable second crop of 16 mg, mp 97°–100° C. (preliminary softening). The structure was confirmed by 200 MHz NMR ($CDCl_3$) and mass spectrum.

Analysis ($C_{34}H_{51}N_5O_7S$)

Calcd: C, 60.60; H, 7.63; N, 10.39; Found: C, 60.43; H, 7.55; N, 10.55

EXAMPLE 5

4-[[(2R,3S)-3-(Boc-L-phenylalanyl-L-histidylamino)-4-cyclohexyl-2-hydroxy-1-butyl-]thio]acetamido]methyl]pyridine.

A gelatinous suspension of 65 mg (0.1 mmole) of 2-[[(2R,3S)-3-(Boc-L-phenylalanyl-L-histidylamino)-4-cyclohexyl-2-hydroxy-1-butyl]thio]-acetic acid and 49 mg (0.11 mmole) of "BOP Reagent" in 1.5 ml of dry $CH_2Cl_2$ was stirred at room temperature as 15.3 μl (11.1 mg, 0.11 mmole) of triethylamine was added, resulting in a nearly clear solution. To this was added 11.2 μl (11.9 mg, 0.11 mmole) of 4-(aminomethyl)pyridine. Stirring was continued at room temperature in a stoppered flask. After approximately 15 hours, the gelatinous mixture was rotary evaporated. Thorough trituration of the residue with ether gave a solid, which was collected on a filter and washed successively with ether, $H_2O$, half-saturated aqueous $NaHCO_3$ solution (triturated thoroughly), $H_2O$, and finally ether. The solid was dissolved in methanol and filtered to remove a small amount of insoluble material. Upon evaporation of the filtrate, the residue was leached with 10 ml of hot acetone containing 2% triethylamine. After cooling and standing, the solid was collected on a filter and washed with 98:2 acetone-triethylamine followed by ether to yield 31 mg (42%) of white powder, mp 185°–187° C. dec. (slight preliminary softening), TLC in 80:20:2 $CHCl_3$—MeOH cond. $NH_4OH$. Mass spectrum and 200 MHz NMR (DMSO $d_6$) supported the assigned structure.

Analysis ($C_{38}H_{53}N_7O_6S.0.5 H_2O$)

Calcd: C, 61.26; H, 7.31; N, 13.16; Found: C, 61.48; H, 7.26; N, 12.96

EXAMPLE 6

N-[2-[[(2R,3S)-3-(Boc-L-phenylalanyl-L-histidylamino)-4-cyclohexyl-2-hydroxy-1-butyl]thio]acetyl]-N,N'-dimethylethylenediamine.

To 74 mg (0.11 mmole) of ethyl 2-[[(2R,3S)-3-(Boc-L-phenylalanyl-L-histidylamino)-4-cyclohexyl-2-hydroxy-1-butyl]thio]acetate was added 100 μl of N,N-dimethylethylenediamine. The mixture, which was stirred at room temperature in a stoppered flask, became homogeneous within a few minutes. After 18 hours, the mixture, which had gelled, was triturated thoroughly with hot ether. The resulting solid was collected on a filter and washed several times with ether, triturating thoroughly each time. This yielded 68 mg (86%) of white powder, mp 160°–164° (preliminary softening), virtually homogeneous by TLC (90:10:1 $CHCl_3$—MeOH-cond. $NH_4OH$). Mass spectrum and 200 MHz NMR (DMSO $d_6$) were in accord with the assigned structure.

Analysis: ($C_{36}H_{57}N_7O_6S.0.5H_2O$)

Calcd: C, 59.64; H, 8.06; N, 13.53; Found: C, 59.50; H, 7.73; N, 13.48

EXAMPLE 7

4-[2-[[(2R,3S)-3-(t-Butoxycarbonylamino)-4-cyclohexyl-2-hydroxy-1-butyl]thio]acetyl]-1-methylpiperazine.

A solution of 0.96 g (2.47 mmole) of ethyl 2-[[(2R,3S)-3-(t-butoxycarbonylamino)-4-cyclohexyl-2-hydroxy-1-butyl]thio]acetate in 3 ml of 1-methylpiperazine was stirred at 80° C. under $N_2$ for 25 hours. The cooled solution was taken up in 100 ml of ethyl acetate and washed with $2 \times 75$ ml of saturated aqueous $NH_4Cl$ solution followed by $1 \times 75$ ml of saturated NaCl solution. The organic phase was dried over $MgSO_4$, filtered, and concentrated to an oil, which upon further drying in vacuo (oil pump) gave 1.1 g (100%) of a stiff foam showing satisfactory purity by TLC (95:5:0.5 $CHCl_3$—MeOH— concd. $NH_4OH$). The structure was confirmed by 300 MHZ NMR ($CDCl_3$)and mass spectrum.

EXAMPLE 8

4-[2-[[(2R,3S)-3-(Boc-L-phenylalanyl-$N^{im}$-Boc-L-histidylamino)-4-cyclohexyl-2-hydroxy-1-butyl]thio]acetyl]-1-methylpiperazine.

To 550 mg (1.24 mmole) of 4-[[(2R,3S)-3-(t-butoxycarbonylamino)-4-cyclohexyl-2-hydroxy-1-butyl]thio]acetyl]-1-methylpiperazine was added 6 ml of methanol freshly saturated with HCl gas at room temperature. The solution was stirred at room temperature under a drying tube. After 10 minutes, TLC (90:10:1

CHCl$_3$—MeOH-concd. NH$_4$OH) showed complete disappearance of starting material. The solution was evaporated to dryness in a stream of N$_2$. The residual oil was twice re-concentrated from methanol and dried in vacuo (oil pump, KOH trap) at 35°-40° C. The residue was treated with 8 ml of dry CH$_2$Cl$_2$ and 346 μl (2.48 mmole) of triethylamine, and the resulting solution was concentrated in vacuo. To the residue were added 585 mg (1.24 mmole) of Boc-L-phenylalanyl-N$^{im}$-Boc-L-histidine, 548 mg (1.24 mmole) of "BOP Reagent", 8 ml of dry CH$_2$Cl$_2$ and 172 μl (1.24 mmole) of fresh triethylamine. The solution was stirred at room temperature under N$_2$ for 3 hours and then concentrated in vacuo. The residue was dissolved in 40 ml of ethyl acetate and washed successively with 2×50 ml of saturated aqueous NH$_4$Cl solution, 40 ml of saturated Na$_2$CO$_3$ solution, and 40 ml of saturated NaCl solution. The ethyl acetate fraction was dried over MgSO$_4$, filtered, and evaporated to dryness. The residue was purified by chromatography on a column of silica gel (48×2.4 cm), eluting with 98:2:0.18:0.02 and then 95:5:0.45:0.05 CH$_2$Cl$_2$—MeOH—H$_2$O-concd. NH$_4$OH. Concentration of the product fraction and further drying in vacuo (oil pump) gave 325 mg (32%) of a yellowish stiff foam which was of satisfactory purity by TLC (90:10:1:0.1 CH$_2$Cl$_2$—MeOH—H$_2$O-concd. NH$_4$OH). Structure and purity were confirmed by 200 MHz NMR (CDCl$_3$) and mass spectrum.

Analysis: (C$_{42}$H$_{65}$N$_7$O$_8$S.1.33 H$_2$O)

Calcd: C, 59.20; H, 8.00; N, 11.51; Found: C, 59.60; H, 7.84; N, 11.35

EXAMPLE 9

4-[2-[[(2R,3S)-3-(Boc-L-phenylalanyl-L-histidylamino)-4-cyclohexyl-2-hydroxy-1-butyl]thio]acetyl]-1-methylpiperazine.

A filtered solution of 245 mg (0.3 mmole) of 4-[[(2R,3S)-3-(Boc-L-phenylalanyl-N$^{im}$-Boc-L-histidylamino))-4-cyclohexyl-2-hydroxyl-1-butyl]thio]acetyl]-1-methylpiperazine in 4 ml of methanol was treated with a stream of ammonia gas for several minutes. The flask was then stoppered, and the solution was stirred at room temperature. After 3 hours, when TLC (90:10:1 CHCl$_3$—MeOH concd. NH$_4$OH) indicated complete conversion to product, the solvent was removed by evaporation in a stream of N$_2$ at 35° C. The residue was triturated with hot ether to give a white solid, which was collected on a filter, washed with ether, and dried in vacuo (oil pump) to give 153 mg (70%), mp >106° C. dec. The structure was confirmed by 200 MHz NMR (DMSO d$_6$) and mass spectrum.

Analysis: (C$_{37}$H$_{57}$N$_7$O$_6$S.H$_2$O)

Calcd: C, 59.57; H, 7.97; N, 13.15; Found: C, 59.43; H, 7.78; N, 12.86

EXAMPLE 10

Ethyl (S)-2-Mercapto-4-methylpentanoate

A solution of 7.2 g (48.6 mmole) of (S)-2-mercapto-4 methylpentanoic acid [J. A. Yankeelov, Jr., K. F. Fok, and D. J. Carothers, *J. Org Chem.*, 43, 1623 (1978)] and 219 mg of p-toluenesulfonic acid in 12 ml of absolute ethanol and 12 ml of CHCl$_3$ was stirred under reflux with collection of liberated H$_2$O in a Dean-Stark trap pre-filled with CHCl$_3$. After 4 hours, the solution was cooled, diluted with an equal volume of CHCl$_3$, and washed successively with H$_2$O, saturated aqueous NaHCO$_3$ solution, and H$_2$O. The organic phase was dried over MgSO$_4$, filtered, and concentrated to give 6.90 g (81%) of an oil, [α]$^{20}_D$ −19.0° (c 2, ether), TLC in 9:1 hexane-ethyl acetate. The structure was verified by 200 MHz NMR (CDCl$_3$).

EXAMPLE 11

Ethyl (2S)-2-[[(2R,3S)-3-(t-Butoxycarbonylamino)-4-cyclohexyl-2-hydroxy-1-butyl]thio]-4-methylpentanoate A solution of 2.85 g (10.6 mmole) of (2R,3S) 3-(t-butoxycarbonylamino)-4-cyclohexyl-1,2-epoxybutane, 1.86 g (10.6 mmole) of ethyl (S)-2-mercapto-4-methylpentanoate, and 1.48 ml (1.07 g. 10.6 mmole) of triethylamine in 40 ml of absolute ethanol was stirred overnight at room temperature under N$_2$. The solution was concentrated in vacuo. The residue was taken up in CH$_2$Cl$_2$ and washed with 0.2N HCl followed by saturated aqueous NaCl solution. The organic phase was dried over MgSO$_4$, filtered, and rotary evaporated. The residual oil was chromatographed on a column of silica gel (57×4.3 cm) packed in hexane (elution with 7:1 and then 4:1 hexane ethyl acetate). Concentration of clean product fractions yielded 4.02 g (85%) of an oil, [α]$^{20}_D$ −63.9°, TLC in 4:1 hexane-ethyl acetate. Mass spectrum and 200 MHz NMR confirmed the structure.

EXAMPLE 12

Ethyl (2S)-2-[[(2R,3S)-3-(Boc-L-phenylalanyl-N$^{im}$-Boc-L-histidylamino)-4-cyclohexyl-2-hydroxy-1-butyl]thio]4-methylpentanoate.

To 1.11 g (2.5 mmole) of ethyl (2S)-2-[[(2R,3S) 3-(t-butoxycarbonylamino)-4-cyclohexyl-2-hydroxy-1-butyl]thio]-4-methylpentanoate was added 13 ml of absolute ethanol, freshly saturated with HCl at room temperature. After 15 minutes, when TLC (4:1 hexane-ethyl acetate) showed complete disappearance of starting material, the solution was evaporated in . a stream of N$_2$ while being stirred at 35° C. The residue was twice re-concentrated from ethanol and then dried in vacuo (oil pump, KOH trap). It was then taken up in 17 ml of dry CH$_2$Cl$_2$ and treated with 0.70 ml (0.51 g, 5 mmole) of triethylamine. The resulting solution was again concentrated and dried in vacuo (oil pump) with only slight warming. The residue was treated with 1.19 g (2.5 mmole) of Boc-L-phenylalanyl-N$^{im}$-Boc-L-histidine, 1.11 g (2.5 mmole) of "BOP Reagent", 0.35 ml (2.5 mmole) of triethylamine, and 20 ml of dry CH$_2$Cl$_2$. This solution was stirred under N$_2$ at room temperature for 4 hours and then concentrated in vacuo. The residue was dissolved in 100 ml of ethyl acetate and washed successively with 50 ml of H$_2$O, 3×50 ml of saturated NaHCO$_3$ solution, and 50 ml of saturated NaCl solution. The ethyl acetate layer, after drying over MgSO$_4$, was filtered and concentrated. The residual foam was chromatographed on a column of silica gel (63×3.5 cm) packed in CH$_2$Cl$_2$ (elution with 99:1 and then 98:2 CH$_2$Cl$_2$-isopropanol. Concentration of clean product fractions yielded 1.17 g (56%) of a solid, mp 82°-83° C., TLC in 97:3 isopropanol. Mass spectrum and 200 MHz NMR (CDCl$_3$) confirmed the assigned structure.

Analysis: (C$_{43}$H$_{67}$N$_5$O$_9$S.0.5H$_2$O)

Calcd: C, 61.55; H, 8.17; N, 8.35; Found: C, 61.49; H, 8.13; N, 8.35

EXAMPLE 13

Ethyl
(2S)-2-[[(2R,3S)-3-(Boc-L-phenylalanyl-L-histidylamino)-4-cyclohexyl-2-hydroxy-1-butyl]-thio]-4-methylpentanoate.

A solution of 86 mg (0.1 mmole) of ethyl (2S)-2-[[(2R,3S)-3-(Boc-L-phenylalanyl-N$^{im}$-Boc-L-histidylamino)-4-cyclohexyl-2-hydroxy-1-butyl]-thio]-4-methylpentanoate in 4 drops of ethanol was treated with 2 drops of hydrazine hydrate and stirred at room temperature under N$_2$ for 1 hour. The solution was partitioned between ethyl acetate (50 ml) and 0.2N HCl (50 ml). The ethyl acetate phase was washed with 50 ml of saturated NaCl solution, then dried over MgSO$_4$, filtered, and concentrated to dryness. Chromatography of the residue on a column of silica gel (18×1.6 cm; elution with 97:3 and then 95:5 CH$_2$Cl$_2$-ethanol) and concentration of the product fractions afforded 44 mg of solid, mp >82° C. (gradual dec.) homogeneous by TLC in 9:1 CH$_2$Cl$_2$-ethanol. Mass spectrum and 200 MHZ NMR (CDCl$_3$) were in agreement with the assigned structure.

EXAMPLE 14

4-[2-[[(2RS)-2-[[(2R,3S)-3-(Boc-L-phenylalanyl-L-histidylamino)-4-cyclohexyl-2-hydroxy-1-butyl]thio]methylpentanoyl]-4-methylpentanoyl]amino]ethyl]morpholine.

A solution of 105 mg (0.125 mmole) of ethyl (2S)-2-[[(2R,3S)-3-(Boc-L-phenylalanyl-N$^{im}$-Boc-L-histidylamino)-4-cyclohexyl-2-hydroxy-1-butyl]thio]-4-methylpentanoate in 4 ml of 4-(2-aminoethyl)-morpholine was stirred under N$_2$ at 80° C. for 4 days. The cooled solution was diluted with 40 ml of ethyl acetate and washed with 40 ml of saturated NH$_4$Cl solution followed by 40 ml of saturated NaCl solution. The ethyl acetate phase was dried over MgSO$_4$, filtered, and concentrated in vacuo. The residue was chromatoqraphed on a column of silica gel (21×2 cm) packed in CH$_2$Cl$_2$ (elution with a gradient of 4–8% methanol in CH$_2$Cl$_2$). The residue from concentration of the product fractions was taken up in CH$_2$Cl$_2$, filtered through Celite, and again concentrated to give 49 mg of white solid, mp 105°-106° C., $[\alpha]_D^{20}$ −17.0° (c 2, CH$_2$Cl$_2$), TLC in 9:1 CHCl$_3$ methanol. The structure was confirmed by 200 MHz NMR (DMSO-d$_6$). The product derived from reaction of the correspondinq (R)-2-mercaptopentanoate derivative with 4-(2-aminoethyl)morpholine had identical rotation and NMR spectrum, indicating that epimerization of the isobutyl substituent α to the carbonyl had occurred during the reaction.

Analysis: (C$_{42}$H$_{67}$N$_7$O$_7$S.0.25CH$_2$Cl$_2$)

Calcd: C, 60.75; H, 8.14; N, 11.74; Found: C, 60.70; H, 8.33; N, 11.37

EXAMPLE 15

Ethyl
[[(2R,3S)-3-(Boc-L-phenylalanyl-N$^{im}$-Boc-L-histidylamino)-4-cyclohexyl-2-hydroxy-1-butylsulfinyl]acetate A solution of 150 mg (0.194 mmole) of ethyl [[(2R,3S)-3-(Boc-L-phenylalanyl-N$^{im}$-Boc-L-histidylamino)-4-cyclohexyl-2-hydroxy-1-butyl]thio]-acetate and 44 mg (approx. 0.21 mmole) of 80–85% m-chloroperoxybenzoic acid in 3 ml of CH$_2$Cl$_2$ was stirred at room temperature for 4.5 hours and then partitioned between ethyl acetate (20 ml) and saturated aqueous Na$_2$CO$_3$ (20 ml). The ethyl acetate layer was washed twice more with saturated Na$_2$CO$_3$, then dried over MgSO$_4$, filtered, and concentrated in vacuo. The residue was chromatographed on a column of silica gel (37×2.1 cm) packed in CH$_2$Cl$_2$ (elution with a gradient of 2–8% isopropanol in CH$_2$Cl$_2$). Concentration of the product fractions yielded an oil which solidified upon drying in vacuo (oil pump): 104 mg (68%), mp 78°-83° C. (preliminary softening), homogeneous by TLC in 9:1 CH$_2$Cl$_2$—MeOH. The structure was confirmed by 300 MHZ NMR (CDCl$_3$) and mass spectrum.

EXAMPLE 16

4-[[(2R,3S)-3-(Boc-L-phenylalanyl-L-histidylamino)-4-cyclohexyl-2-hydroxy-1-butyl]-sulfinyl]acetyl]amino]ethyl]morpholine A solution of 100 mg (0.127 mmole) of ethyl [[(2R,3S)-3 (Boc-L-phenylalanyl-N$^{im}$-Boc-L-histidylamino)-4-cyclohexyl-2-hydroxy-1-butyl]sulfinyl]-acetate in 1 ml of 4 (2 aminoethyl)morpholine was stirred under N$_2$ overnight at room temperature and then partitioned between ethyl acetate (20 ml) and saturated aqueous NH$_4$Cl. Because of some insoluble organic material which separated, 3 ml of tetrahydrofuran was added, and the mixture was again shaken. The organic phase was washed with saturated NaCl solution, then dried over MgSO$_4$, filtered, and concentrated in vacuo. The residual solid was dissolved with warming in 98:2:0.2 CH$_2$Cl$_2$—MeOH-concd. NH$_4$OH and applied to a column of silica gel (17.5×1.9 cm) packed in CH$_2$Cl$_2$. Elution with 95:5:0.5 and then 90:10:1 CH$_2$Cl$_2$—MeOH-concd. NH$_4$OH and concentration of the product fractions yielded 25 mg (25%) of white solid, mp 188°-190° C. dec, TLC in 10:1 CH$_2$Cl$_2$—MeOH concd. NH$_4$OH. The 300 MHz NMR spectrum and mass spectrum were in agreement with the assigned structure.

Analysis: (C$_{38}$H$_{59}$N$_7$O$_8$S.1.75H$_2$O)

Calcd: C, 56.66; H, 7.82; N, 12.17; Found: C, 56.76; H, 7.75; N, 12.12

EXAMPLE 17

Ethyl 2-[[(2R,3S)-3-(t Butoxycarbonylamino)-4-cyclohexyl-2-hydroxy-1-butyl]sulfonyl]acetate A solution of 389 mg (1 mmole) of ethyl 2-[[(2R,3S)-3-(t butoxycarbonylamino-4-cyclohexyl-2-hydroxy-1-butyl]thio]acetate in 4 ml of CH$_2$Cl$_2$ stirred at room temperature was treated with 518 mg (3 mmole) of m chloroperoxybenzoic acid. A thick precipitate soon separated. After 1.5 hours the mixture was partitioned between 50 ml of ethyl acetate and 50 ml of saturated aqueous Na$_2$CO$_3$. The ethyl acetate layer was washed with an additional portion of saturated Na$_2$CO$_3$, then dried over Na$_2$SO$_4$, filtered and concentrated to yield 373 mg (89%) of white solid, mp 102°-104° C., TLC in 19:1 CH$_2$Cl$_2$—MeOH. The structure was corroborated by mass spectrum and 200 MHz NMR (CDCl$_3$).

Analysis: (C$_{19}$H$_{35}$NO$_7$S)

Calcd: C, 54.13; H, 8.37; N, 3.32; Found: C, 54.33; H, 8.15; N, 3.19

EXAMPLE 18

Ethyl 2-[[(2R,3S) 3 (Boc-L-phenylalanyl-N$^{im}$-Boc-L-histidylamino)-4-cyclohexyl-2-hydroxy-1-butyl]-sulfonyl]acetate.

By the procedure described above (see Example 3), ethyl 2-[[(2R,3S)-3-(t-butoxycarbonylamino)-4-cyclohexyl-2-hydroxy-1-butyl] -sulfonyl]acetate was deprotected and the resulting amine reacted with Boc-L-phenylalanyl-N$^{im}$-Boc-L-histidine. Chromatographic purification on a column of silica gel (elution with a gradient of 1–3% ethanol in CH$_2$Cl$_2$) gave a 47% yield of the product as a stiff, white foam, homogeneous by TLC in 97:3 CH$_2$Cl$_2$-ethanol. The 200 MHz NMR and mass spectrum were in accord with the assigned structure.

Analysis: (C$_{39}$H$_{59}$N$_5$O$_{11}$S.0.5H$_2$O)

Calcd: C, 57.47; H, 7.42; N, 8.59; Found: C, 57 40; H, 7.69; N, 8.70

EXAMPLE 19

4-[2-[[2-[[(2R,3S)-3-(Boc-L-phenylalanyl-L-histidylamino)-4-cyclohexyl-2-hydroxy-1-butyl]-sulfonyl]amino]ethyl]morpholine A solution of 100 mg (0.123 mmole) of ethyl 2-[[(2R,3S)-3-(Boc-L-phenylalanyl-N$^{im}$-Boc-L-histidylamino)-4-cyclohexyl-2-hydroxy-1-butyl]sulfonyl]acetate in 2 ml of 4-(2 aminoethyl)-morpholine was stirred at room temperature in a stoppered flask for 2 days and then diluted to 75 ml with ethyl acetate. This solution was washed with 2×50 ml of saturated aqueous NH$_4$Cl followed by 50 ml of saturated NaCl. The ethyl acetate fraction was dried over MgSO$_4$, filtered, and concentrated in vacuo. The residue was chromatographed on a column of silica gel (26×2.1 cm) packed in CH$_2$Cl$_2$ (elution with a gradient of 3–10% methanol in CH$_2$Cl$_2$). Concentration of the product fractions yielded 68 mg (70%) of a white solid having an indistinct melting point. Structure and purity were confirmed by TLC (90:10:1 CH$_2$Cl$_2$—MeOH-concd. NH$_4$OH), 200 MHz NMR, and mass spectrum.

EXAMPLE 20

4-[2-[2-[[(2R,3S)-3-[t-Butoxycarbonylamino)-4-cyclohexyl-2-hydroxy-1-butyl]sulfonyl]acetamido]ethyl]-morpholine A mixture of 1.98 g (4.7 mmole) of ethyl 2-[[(2R,3S) 3-(t butoxycarbonylamino)-4-cyclohexyl-2-hydroxy-1-butyl]sulfonyl]acetate and 2.3 ml of 4-(2-aminoethyl)-morpholine was stirred under N$_2$ at room temperature for 2 days. The light amber syrup was dissolved in 75 ml of ethyl acetate and washed with 3×30 ml of saturated aqueous NH$_4$Cl followed by 30 ml of H$_2$O. The ethyl acetate fraction was dried over Na$_2$SO$_4$, filtered, and concentrated. Further drying in vacuo (oil pump) gave 2.19 g (92%) of a nearly colorless, stiff foam or glass. Structure and purity were confirmed by 300 MHz NMR (CDCl$_3$), mass spectrum, and TLC (9:1 CHCl$_3$—MeOH).

Analysis: (C$_{23}$H$_{43}$N$_3$O$_7$S)

Calcd: C, 54.63; H, 8.57; N, 8.31. Found: C, 54.48; H, 8.40; N, 8.11.

EXAMPLE 21

4-[2-[2-[[(2R,3S)-3-[N$^{\alpha}$,N$^{im}$-Bis(t-butoxycarbonyl)-L-histidylamino]-4-cyclohexyl-2-hydroxy-1-butyl]sulfonyl]acetamido]ethyl]morpholine.

To 1.01 g (2 mmole) of 4-[2-[[(2R,3S)-3-(t-butoxycarbonylamino)-4-cyclohexyl-2-hydroxy-1-butyl]sulfonyl]acetamido]ethyl]morpholine was added 4 ml of anhydrous trifluoroacetic acid, and the mixture was stirred at room temperature under N$_2$. Vigourous gas evolution occurred initially but ceased within a few minutes. After 1.5 hours, the solution . was evaporated in a stream of N$_2$ and then dried further in vacuo (oil pump, KOH trap) at room temperature. The residual viscous oil was dissolved in 70 ml of ethyl acetate and washed with 2×50 ml of saturated aqueous Na$_2$CO$_3$. The ethyl acetate phase was dried over Na$_2$SO$_4$, filtered, and concentrated in vacuo (finally on oil pump) at room temperature. To the light amber residual glass were added 710 mg (2 mmole) of N$^{\alpha}$,N$^{im}$-bis(t-butoxycarbonyl)-L-histidine (freshly prepared from the corresponding dicyclohexylamine salt by partitioning between CH$_2$Cl$_2$ amd 5% aqueous citric acid), 884 mg (2 mmole) of "BOP Reagent", 10 ml of dry CH$_2$Cl$_2$ and 278 μl (202 mg, 2 mmole) of triethylamine. The resulting solution was stirred at room temperature in a stoppered flask for 3 days and then concentrated in vacuo. The residue was chromatographed on a column of silica gel (65×3.5 cm; elution with a gradient of 3% to 7.5% methanol in CH$_2$Cl$_2$). Because the material obtained upon concentration of the product fractions still contained some triethylamine, it was dissolved in 30 ml of ethyl acetate and washed with 2×30 ml of saturated aqueous NH$_4$Cl. The ethyl acetate fraction was dried over Na$_2$SO$_4$, filtered, and concentrated in vacuo (finally on oil pump at 85° C.) to give 895 mg (60%) of a cream-colored, stiff foam. Purity and structure were confirmed by TLC (9:1 CHCl$_3$—MeOH), 300 MHz NMR CDCl$_3$), and mass spectrum.

EXAMPLE 22

(S)-2-[(t-Butylsulfonyl)methyl]-3-phenylpropionic acid N-hydroxysuccinimide ester A mixture of 511 mg (1.8 mmole) of (S)-2-[(t butylsulfonyl)methyl]-3-phenylpropionic acid [P. Buhlmayer et al., J. Med. Chem., 31, 1839 (1988)] 207 mg (1.8 mmole) of N-hydroxysuccinimide, 371 mg (1.8 mmole) of N,N'-dicyclohexylcarbodiimide, and 3.6 ml of dry acetonitrile was stirred at room temperature in a stoppered flask for 3 days. The thick mixture was diluted with 25 ml of ethyl acetate, allowed to stand for a few minutes, and then filtered to remove dicyclohexylurea. The filtrate was washed with 25 ml of saturated aqueous NaHCO$_3$, then dried over MgSO$_4$, filtered, and concentrated in vacuo. Crystallization of the residue from a small volume of ethyl acetate yielded 429 mg of colorless crystals, mp 154°–155.5° C. Evaporation of the mother liquor gave a solid, which was triturated and washed with ether, Recrystallization of this material from a small volume of ethyl acetate provided 93 mg of a usable second crop of colorless crystals, mp 151°–155°, for a total yield of 522 mg (76%). The structure and purity were confirmed by mass spectrum, 300 MHz NMR (CDCl$_3$) and TLC (19:1 CH$_2$Cl$_2$—MeOH).

Analysis: (C$_{18}$H$_{23}$NO$_6$S)

. Calcd: C, 56.67; H, 6.08; N, 3.67; Found: C, 56.40; H, 6.17; N, 3.77

EXAMPLE 23

4-[2-[2-[[(2R,3S)3-[N$^\alpha$-[(S)-2-[(t-Butylsulfonyl)-methyl]-3-phenylpropionyl]-L-histidylamino]-4-cyclohexyl-2-hydroxy-1-butyl]sulfonyl]-acetamido]ethyl]morpholine To 802 mg (1.08 mmole) of 4-[2-[2-[[(2R,3S)-3-[N$^\alpha$,-N$^{im}$-bis(t-butoxycarbonyl)-L-histidylamino]-4-cyclohexyl-2-hydroxy-1-butyl]sulfonyl]acetamido]-ethyl]morpholine was added 3.2 ml of anhydrous trifluoroacetic acid, and the mixture was stirred under N$_2$ at room temperature. Gas evolution was observed initially, and a clear solution was obtained within a few minutes. After 4 hours, the solution was evaporated in a stream of N$_2$. The residual oil was re concentrated 3x from ethanol and dried in vacuo (oil pump, KOH trap). The resulting tan, stiff foam was treated with 412 mg (1.08 mmole) of (S)-2-[(t-butylsulfonyl)methyl]-3-phenylpropionic acid N-hydroxysuccimide ester, 902 μl (654 mg, 6.48 mmole) of triethylamine, and 3.2 ml of dry CH$_2$Cl$_2$. The mixture was stirred at room temperature in a stoppered flask, and a clear solution was soon obtained. After 15.5 hours, an additional 151 μl (1.08 mmole) of triethylamine was added. After 39 hours, the solution was concentrated in vacuo at room temperature to give a viscous residual oil. A solution of this material in a mixture of 30 ml of ethyl acetate and 20 ml of tetrahydrofuran was washed with 2×20 ml of saturated aqueous NaHCO$_3$ and then with 3×20 ml of saturated NH$_4$Cl solution. The organic phase was dried over Na$_2$SO$_4$, filtered, and concentrated in vacuo. The residual foam was chromatographed on a column of silica gel (64.5×3.5 cm) packed in CH$_2$Cl$_2$ (eluted successively with 95:5:0.5, 94:6:0.5, and 92.5:7.5:0.5 CH$_2$Cl$_2$—MeOH-concd NH$_4$OH). Since the material isolated upon concentration of the cleanest product fractions was still not pure, it was dissolved in CH$_2$Cl$_2$ (10 ml) and applied to 20 1000-μ silica gel prep. TLC plates (20×20 cm). The plates were developed in 85:15:1.5 CH$_2$Cl$_2$—MeOH concd. NH$_4$OH, and the isolated product bands were extracted with the same solvent. The residue from concentration of the extracts was taken up in CH$_2$Cl$_2$, filtered, and re-concentrated. Further drying in vacuo (oil pump) at 65°-70° C. yielded 373 mg (43%) of a glass, which upon scraping went to a powder, mp >120° C. (gradual, after preliminary softening). Structure and purity were confirmed by mass spectrum, 300 MHz NMR (CDCl$_3$), and TLC (90:10:1 CHCl$_3$—MeOH-concd. NH$_4$OH).

Analysis: (C$_{38}$H$_{60}$N$_6$O$_9$S$_2$.H$_2$O)
Calcd: C, 55.18: H, 7.56: N, 10.16; Found: C, 55.30: H, 7.32: N, 10.14

What is claimed is:

1. A compound which is 2-[X-thio]acetic acid in which X means [(2R,3S)-3-(Boc-L-phenylalanyl-L-histidylamino)-4-cyclohexyl-2-hydroxy-1-butyl].
2. A compound which is ethyl 2-[X-thio]acetate and X is as defined in claim 1.
3. A compound which is 4-[[2-[X-thio]acetamido]methyl]pyridine in which X is as defined claim 1.
4. A compound which is 4-[2-[2-[X-thio]acetamido]ethyl]morpholine in which X is as defined in claim 1.
5. A compound which is N-[2-[X-thio]acetyl]-N',N'-dimethylethylenediamine and X is a defined in claim 1.
6. A compound which is 4-[2-[X-thio]acetyl]-1-methylpiperazine in which X is as defined in claim 1.
7. A compound which is 3-[2-[X-thio]acetamido]quinuclidine in which X is as defined in claim 1.
8. A compound which is ethyl (2S)-2-[X-thio]-4-methylpentanoate in which X is as defined in claim 1.
9. A compound which is ethyl (2R)-2-[X-thio]-4-methylpentanoate in which X is as defined in claim 1.
10. A compound which is 4-[2-[[(2RS)-2-[X-thio]-4-methylpentanoyl]amino]-ethyl]morpholine in which X is as defined in claim 1.
11. A compound which is 4-[2-[2-[X-sulfinyl]acetamido]ethyl]morpholine in which X is as defined in claim 1.
12. A compound which is 4-[2-[2-[X-sulfonyl]acetamido]ethyl]morpholine in which X is as defined in claim 1.
13. A compound which is 4-[2-[X-sulfonyl]acetyl]-1-methylpiperazine in which X is as defined claim 1.
14. A compound which is 1-benzyl-4-[2-[X-sulfonyl]acetamido]piperidine in which X is as defined in claim 1.
15. A compound which is 3-[2-[X-sulfonyl]acetamido]quinuclidine N-oxide in which X is as defined in claim 1.
16. A compound which is 4-[2-[[(2RS)-2-[X-sulfinyl]-4 methylpentanoyl]amino]ethyl}morpholine in which X is as defined in claim 1.
17. A compound which is 4-[2-[[(2RS)-2-[X-sulfonyl]-4 methylpentanoyl]amino]ethyl}morpholine in which X is as defined in claim 1.
18. A compound which is 4-[2-[2-[[(2R,3S)-3-[N$^\alpha$-[(S)-2-[(t-butysulfonyl)-methyl]-3-phenylpropionyl]-L-histidylamino]-4-cyclohexyl-2-hydroxy-1-butyl]sulfonyl]acetamido]-ethyl]morpholine.

* * * * *